United States Patent [19]

Satzinger et al.

[11] 4,018,775

[45] Apr. 19, 1977

[54] 5-PHENYL-THIAZOLIDIN-4-ONE DERIVATIVES

[75] Inventors: Gerhard Satzinger, Denzlingen; Manfred Herrmann, St. Peter, both of Germany

[73] Assignee: Warner-Lambert Company, Morris Plains, N.J.

[22] Filed: Apr. 30, 1975

[21] Appl. No.: 572,987

[30] Foreign Application Priority Data

May 16, 1974 Germany .......................... 2423725

[52] U.S. Cl. .................. 260/293.68; 260/306.7 R; 424/267; 424/270
[51] Int. Cl.² ...................................... C07D 277/34
[58] Field of Search ............... 260/293.68, 306.7 R

[56] References Cited

UNITED STATES PATENTS 3,072,653   1/1963   Satzinger ..................... 260/293.68

*Primary Examiner*—Henry R. Jiles
*Assistant Examiner*—Robert T. Bond
*Attorney, Agent, or Firm*—Albert H. Graddis; Frank S. Chow; George M. Yahwak

[57] ABSTRACT

The present invention is concerned with new pharmacologically effective 5-phenyl-thiazolidin-4-one derivatives and with the preparation thereof. These compounds are useful for treating liver dysfunctions.

8 Claims, No Drawings

5-PHENYL-THIAZOLIDIN-4-ONE DERIVATIVES

U.S. Pat. Nos. 3,182,063 and 3,072,653, as well as Liebigs Annalen der Chemie, 665, 150–165/1963, describe certain substituted 2-methylene-thiazolidin-4-ones which have an analgesic, sedative and anti-inflammatory action. Some of these compounds are also known to possess a certain choleretic and diuretic action. The compounds according to the present invention differ from the known compounds in that they are substituted in the 5-position by a phenyl radical.

The introduction of this radical and changing of the substituents leads, surprisingly, to compounds which are valuable pharmaceuticals having a superior hepatoprotective and curative anti-hepatotoxic effect and, especially in the case of a prolonged treatment, do not exhibit any undesired choleretic or other side effects. Consequently, the new compounds according to the present invention are outstandingly useful for prolonged liver therapy.

The new compounds according to the present invention are 5-phenyl-thiazolidin-4-ones of the general formula:

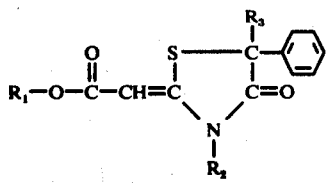

wherein $R_1$ is a lower alkyl radical, $R_2$ is a lower alkyl or aralkyl radical and $R_3$ is a lower alkyl or aralkyl radical or is a basic radical of the general formula:

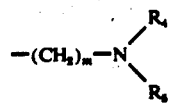

in which $m$ is 0, 1, 2 or 3 and $R_4$ and $R_5$ which can be the same or different, are lower alkyl or hydroxyalkyl radicals or $R_4$ and $R_5$, together with the nitrogen atom to which they are attached, represents a saturated heterocyclic ring containing 4 to 6 carbon atoms, as well as the pharmacologically compatible salts of those compounds in which $R_3$ contains a basic radical.

The lower alkyl and hydroxyl alkyl radicals can be straight or branched and contain up to 6 carbons. Aralkyl radicals within the scope of this invention contain an aromatic ring, preferably a benzene ring, and an alkylene radical of up to 3 carbon atoms.

Those compounds of general formula (I) are preferred in which $R_1$ is an alkyl radical of up to 3 carbon atoms; $R_2$ is an alkyl radical of up to 3 carbon atoms or a benzyl radical; and $R_3$ is an alkyl radical of up to 3 carbon atoms, a benzyl radical or a basic radical of the above-given general formula in which $m$ is 0 or 2 and $R_4$ and $R_5$, which can be the same or different, are alkyl or hydroxyalkyl radicals containing up to 3 carbon atoms or $R_4$ and $R_5$, which can be the same or different, are alkyl or hydroxyalkyl radicals containing up to 3 carbon atoms or $R_4$ and $R_5$, together with the nitrogen atom to which they are attached, is a piperidine or pyrrolidine ring.

Examples of lower alkyl radicals include methyl, ethyl, n-propyl, isopropyl, n-butyl, isobutyl, n-pentyl and n-hexyl radicals. The hydroxyalkyl radicals are the radicals of corresponding primary or secondary aliphatic alcohols.

Those preferred compounds include those in which $R_1$ is an ethyl radical, $R_2$ is a methyl or ethyl radical and $R_3$ is an ethyl, piperidino or pyrrolidino radical and the salts thereof with pharmacologically compatible acids.

The new compounds according to the present invention can be prepared in the following manner:

a. for the case in which $R_3$ contains an alkylene group, which is to be connected to the thiazolidinone ring, a compound of the general formula:

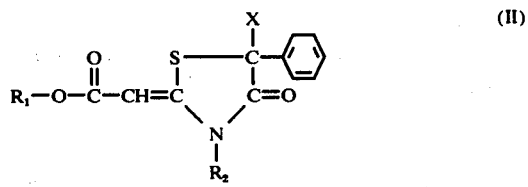

wherein $R_1$ and $R_2$ have the same meanings as above and X is a hydrogen or alkali metal atom, is reacted with a compound of the general formula:

wherein V is a reactive ester group and $R_6$ is a lower alkyl or aralkyl radical or a basic radical of the above-given general formula, in which $R_4$ and $R_5$ have the same meanings as above and $m$ is 1, 2, or 3; or b. for the case in which $R_3$ is an amino group, which is to be connected directly via a nitrogen atom with the thiazolidinone ring, a compound of the general formula:

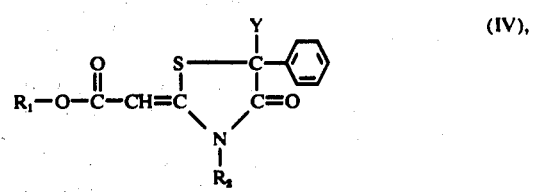

wherein $R_1$ and $R_2$ have the same meanings as above, and Y is a halogen atom, is reacted with a compound of the general formula:

wherein $R_4$ and $R_5$ have the same meanings as above.

The reactive ester groups V can be, for example, halides or sulphates.

Reaction (a) is generally carried out by dissolving an appropriate 3-alkyl-5-phenyl-4-oxo-$\Delta^{2,\alpha}$-thiazolidine-acetic acid ester in a lower aliphatic alcohol, for example, ethanol or tert.-butanol, and, depending upon the reactivity of the radical to be introduced, either reacting directly with compounds (III) in the presence of an acid-binding agent or converted by means of an alkali metal alcoholate in the corresponding alcohol into the intermediate alkali metal salt which is then reacted with a compound of general formula (III). The reaction is preferably carried out at a temperature of 60°–100° C. and is usually completed after 1 to 5 hours.

Reaction (b) can be carried out either in situ, i.e. in the chlorinated hydrocarbon used for the preparation thereof, or after isolation of the intermediate (IV), in diethyl ether, dioxan or benzene at a temperature of 0° to 20° C. The reaction is usually completed within 4 to 20 hours but, in some cases, it is necessary subsequently to heat the reaction mixture under reflux for 0.5 to 1 hour.

The starting materials of general formulae (II) and (IV) can be prepared by reacting a compound of the general formula:

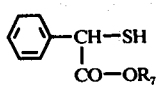
(VI)

in which $R_7$ is a lower alkyl radical, with a nitrile of the general formula:

in which $R_1$ has the same meaning as above, in the presence of a basic catalyst, to give a compound of the general formula:

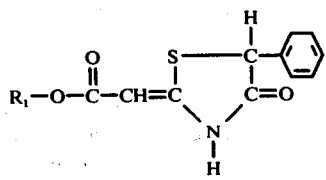
(VIII)

wherein $R_1$ has the same meaning as above, which is then alkylated or benzylated on the more acidic 3-position with appropriate reactive esters, for example, alkyl or benzyl halides, and subsequently either converted into the 5-alkali metal salts in an appropriate alkaline medium or reacted in an inert medium with a free halogen, preferably bromine.

As inert solvents, there are preferably used chlorinated hydrocarbons, for example, carbon tetrachloride. The bromination can be carried out directly with elementary bromine or with N-bromosuccinimide. The reaction time is usually about 1 to 2 hours at temperatures between about 50° C. and 80° C.

The compounds of general formula (VIII) are also novel compounds.

The introduction of the radical $R_2$ can take place at a temperature between about 60° C. and 100° C. and is usually carried out in a polar solvent, for example ethanol or isopropanol, with the addition of a molar or excess amount of an acid acceptor, for example pyridine, triethylamine or potassium carbonate. The time of the reaction is about 1 to 5 hours.

The cyclocondensation of compounds (VI) and (VII) takes place in the manner described in U.S. Pat. Nos. 3,182,063 and 3,072,653.

When the compounds (I) contain a basic amino group, pharmacologically compatible salts can be obtained in the usual manner, for example by neutralization of the free base with pharmacologically compatible inorganic or organic acids.

The compounds of general formula (I) and the salts thereof can be administered enterally or parenterally in admixture with conventional solid or liquid pharmaceutical diluents or carriers. An injection medium, it is preferred to use water which contains the usual additives for injection solutions, for example stabilizing agents, solubilizing agents or buffers. Formulations for oral administration can, if desired, contain flavoring and/or sweetening agents.

The dosage of the new compounds according to the present invention depends upon the nature and severity of the disease to be treated. The individual oral dose is usually of the order of about 50 to 500 mg.

The following Examples are given for the purpose of illustrating the present invention.

EXAMPLE 1

Ethyl 3-methyl-5-ethyl-5-phenyl-4-oxo-$\alpha^{2,\alpha}$-thiazolidine-acetate

A solution of sodium tert.-butylate is prepared by dissolving 1.2 g. sodium chips (0.05 mol) in 150 ml. anhydrous boiling tert.-butanol. 14 g. ethyl 3-methyl-5-phenyl-4-oxo-$\alpha^{2,\alpha}$-thiazolidine-acetate are introduced into this solution, whereafter a solution of 20 ml. ethyl iodide in 100 ml. anhydrous ethanol is added. After heating under reflux for 45 minutes, a yellow solution is formed. After a further 45 minutes, all of the solvent mixture is stripped off in a vacuum and the residue is partitioned between 0.5 liters water and 100 ml. ether. The ethereal phase is dried and distilled, whereafter the residue obtained is then distilled. At a boiling point of 200° C./1 mm.Hg. there is obtained ethyl 3-methyl-5-ethyl-5-phenyl-4-oxo-$\Delta^{2,\alpha}$-thiazolidine-acetate in the form of a highly viscous yellowish oil. IR spectrum: 1712 cm$^{-1}$ (s, lactam ring), 1688 cm$^{-1}$ (s, $\alpha,\beta$-unsaturated ester), 1570 cm$^{-1}$ (CH=C), 1180 cm$^{-1}$ (s, C-O asymmetry), 1040 cm$^{-1}$ (m, C-O symmetry), 795 cm$^{-1}$ (m, H-C=), 695 cm$^{-1}$ (m, phenyl).

Analysis: $C_{16}H_{19}NO_3S$ (M.W. 305.39): Calc.: C 62.93%; H 6.27%; N 4.58%; S 10.50%; Found: 62.70% 6.29%; 4.75%; 10.29%.

The following compounds are prepared in an analogous manner:

methyl 3-methyl-5-ethyl-5-phenyl-4-oxo-$\Delta^{2,\alpha}$-thiazolidine-acetate;

butyl 3-methyl-5-ethyl-5-phenyl-4-oxo-$\Delta^{2,\alpha}$-thiazolidine-acetate; and butyl 3,5-diethyl-5-phenyl-4-oxo-$\Delta^{2,\alpha}$-thiazolidine-acetate.

The compounds used as starting materials are prepared in the following manner:

Into a solution of 10.6 g. (0.1 mol) triethylamine in 210 ml. anhydrous benzene, there is rapidly introduced a mixture of 11.9 g. (0.1 mol) ethyl cyanoacetate and 18.2 g. (0.1 mol) methyl $\alpha$-mercaptophenylacetate, whereafter the reaction mixture is stirred for 18 hours at ambient temperature. Part of the reaction product gradually precipitates out in the form of crystalline platelets which are separated off. The reaction mixture is evaporated to dryness in a vacuum and the residue, together with the precipitated product, recrystallised from benzene. There are obtained 14.6 g. (55.5% of theory) ethyl 5-phenyl-4-oxo-$\Delta^{2,\alpha}$-thiazolidine-acetate; m.p. 177°–178° C.

n-Butyl 5-phenyl-4-oxo-$\Delta^{2,\alpha}$-thiazolidine-acetate is prepared in an analogous manner. In the case of a 0.1 molar batch, there are obtained 21.0 g. (72% of theory) of the product which, after recrystallisation from acetate-water, melts at 137° C.

15.8 g. (0.06 mol) ethyl 5-phenyl-4-oxo$\Delta^{2,\alpha}$-triazolidine-acetate are dissolved in 240 ml. 96% ethanol and stirred under gentle reflux with 9.1 g. (0.66 mol) powdered potassium carbonate. With the further external application of heat, 7.6 g. (0.06 mol) dimethyl sulphate are added dropwise. Subsequently, the reaction mixture is heated under reflux for 1 hour and then introduced into about 0.5 liter hot water. The product which separates out is filtered off and dried and then recrystallised from cyclohexane. There are obtained 12.0 g. (72% of theory) ethyl 3-methyl-5-phenyl-4-oxo-$\Delta^{2,\alpha}$-thiazolidine-acetate, which has a melting point of 112 – 114° C.

n-Butyl 3-methyl-5-phenyl-4-oxo-$\Delta^{2,\alpha}$-thiazolidine-acetate is prepared in an analogous manner. Using a 0.035 molar batch, there are obtained 8.0 g. (74.8% of theory) of product which, after recrystallisation from ligroin, melts at 98° C.

By using diethyl sulphate, there is obtained, for example, in an analogous manner n-butyl 3-ethyl-5-phenyl-4-oxo$\Delta^{2,\alpha}$-thiazolidine-acetate. When using an 0.06 molar batch, the yield is 12.1 g. (63.3% of theory). After recrystallisation from ether/petroleum ether (1:1), the product has a melting point of 84° C.

EXAMPLE 2

Ethyl 5-phenyl-3,5-dibenzyl-4-oxo-$\Delta^{2,\alpha}$-thiazolidine-acetate.

10.5 g. (0.04 mol) ethyl 5-phenyl-4-oxo-$\Delta^{2,\alpha}$-thiazolidine-acetate are dissolved in 180 ml. anhydrous ethanol and mixed with 12.14 g. (0.088 mol) anhydrous powdered potassium carbonate. The reaction mixture is then boiled and stirred. 10.08 g. (0.08 mol) benzyl chloride are gradually added thereto and the reaction mixture then heated under vigorous reflux for 2 hours. While still warm, the reaction mixture is introduced into 0.5 liter hot water and the precipitated product is separated off and taken up in benzene/ethyl acetate (1:1). After removal of the solvent mixture, the residue is digested with ether and recrystallised from methanol. There are obtained 8 g. (42.4% of theory) ethyl 5-phenyl-3,5-dibenzyl-4-oxo-$\Delta^{2,\alpha}$-thiazolidine-acetate, which melts at 154°–156° C.

Analysis: $C_{27}H_{25}NO_3S$ (M.W. 443.57): calc.: C 72.81%; H 5.70%; N 3.36%; S 7.37%; found: 73.10%; 5.69%; 3.16%; 7.73%.

EXAMPLE 3

Ethyl 3-methyl-5-phenyl-5-benzyl-4-oxo-$\Delta^{2,\alpha}$-thiazolidine-acetate.

8.31 g. (0.03 mol) ethyl 3-methyl-5-phenyl-4-oxo-$\Delta^{2,\alpha}$-thiazolidine-acetate and 4.56 g. (0.033 mol) potassium carbonate (anhydrous, powdered) are introduced into 120 ml. anhydrous ethanol. The reaction mixture is heated under reflux and mixed dropwise, within the course of 1.5 hours, with 3.78 g. (0.03 mol) benzyl chloride. Half of the solvent is then distilled off and the residue digested with hot water. It is then extracted with ethyl acetate and the residue of this extract stirred for a few hours with cyclohexane. After recrystallisation from petroleum ether, there are obtained 6.0 g. (54.5% of theory) ethyl 3-methyl-5-phenyl-5-benzyl-4-oxo-$\Delta^{2,\alpha}$-thiazolidine-acetate, which has a melting point of 105°–107° C.

Analysis: $C_{21}H_{21}NO_3S$ (M.W. 367.47): calc.: C 68.63%; N 5.76%; N 3.82%; S 8.73%; found: 68.63%; 5.57%; 3.93%; 9.01%.

EXAMPLE 4

Ethyl 3-methyl-5-phenyl-5-(2-diethylaminoethyl)-4-oxo-$\Delta^{2,\alpha}$-thiazolidine-acetate.

Ethyl 3-methyl-5-phenyl-4-oxo-$\Delta^{2,\alpha}$-thiazolidine-acetate is reacted with diethylaminoethyl chloride in a manner analogous to that described in Example 3. After introducing the reaction mixture in hot water, it is extracted with ethyl acetate. This extract is subsequently shaken out with 2N hydrochloric acid. The hydrochloric acid phase is rendered alkaline with 1N aqueous sodium hydroxide solution and the crude base which separates out is taken up in ether. The ethereal solution is evaporated and the residue obtained is dissolved in isopropanol and the product precipitated by the addition of oxalic acid. The oxalate is separated off and recrystallised from isopropanol. In the case of the use of a 0.025 molar batch, there are obtained 3.5 g. (27% of theory) ethyl 3-methyl-5-phenyl-5-(2-diethylaminoethyl)-4-oxo-$\Delta^{2,\alpha}$-thiazolidine-acetate, which melts at 126°–128° C.

Analysis: $C_{22}H_{30}N_2O_7S$ (oxalate) (M.W. 466.56): calc: C 56.64%; H 6.49%; N 6.00%; S 6.87%; found: 56.53%; 6.27%; 6.04%; 6.58%.

EXAMPLE 5

Ethyl 3-ethyl-5-phenyl-5-N-piperidino-4-oxo-$\Delta^{2,\alpha}$-thiazolidine-acetate.

Starting from ethyl 5-phenyl-4-oxo-$\Delta^{2,\alpha}$-thiazolidine-acetate, there is prepared, in a manner analogous to that described in Example 1, by alkylation with diethyl sulphate, ethyl 3-ethyl-5-phenyl-4-oxo-$\Delta^{2,\alpha}$-thiazolidine-acetate, the yield being 56% of theory. After recrystallisation from cyclohexane, the product melts at 119.5°–120° C.

42.2 g. (0.15 mol) ethyl 3-ethyl-5-phenyl-4-oxo-$\Delta^{2,\alpha}$-thiazolidine-acetate are dissolved in 0.9 liters anhydrous carbon tetrachloride. The solution is heated under reflux and mixed dropwise with 24 g. (7.7 ml., 0.15 mol) bromine. After 1.5 hours, still dissolved hydrogen bromide is driven off by passing in nitrogen. The ethyl 3-ethyl-5-bromo phenyl-4-oxo-$\Delta^{2,\alpha}$-thiazolidine-acetate formed is then, without isolation, reacted with piperidine (35.6 ml., 0.36 mol). Subsequently, the reaction mixture is further heated under reflux for 0.5 hours. Piperidine hydrobromide is then separated off, the filtrate evaporated to dryness and the residue is dissolved in 75 ml. hot isopropanol. The crystals which separate out are collected and recrystallised from ethanol. There are obtained 25.3 g. (45.2% of theory; over two stages) ethyl 3-ethyl-5-phenyl-5-N-piperidino-4-oxo-$\Delta^{2,\alpha}$-thiazolidine-acetate, which has a melting point of 106° C.

Analysis: $C_{20}H_{26}N_2O_3S$ (M.W. 374.52); calc.: C 64.14%; H 7.00%; N 7.48%; S 8.56%; found: 64.28%; 6.71%; 7.66%; 8.71%.

EXAMPLE 6

Ethyl 3-ethyl-5-phenyl-5-(methyl-β-hydroxyethylamino)-4-oxo-$\Delta^{2,\alpha}$-thiazolidine-acetate.

Ethyl 3-ethyl-5-phenyl-4-oxo-$\Delta^{2,\alpha}$-thiazolidine-acetate is reacted with bromine in a manner analogous to that described in Example 5. The ethyl 3-ethyl-5-bromo-5-phenyl-4-oxo-$\Delta^{2,\alpha}$-thiazolidine-acetate thus obtained is then reacted with N-methyl-ethanolamine and the reaction product chromatographed over a column of silica gel with benzene/methanol (9:1). There are obtained 8.5 g (0.1 molar batch corresponding to 28% of theory, over two stages) ethyl 3-ethyl-5-phenyl-5-(methyl-β-hydroxyethylamino)-4-oxo-$\Delta^{2,\alpha}$-thiazolidine-acetate which, after recrystallization from isopropanol/ether (2:1) has a melting point of 117° C.

Analysis: $C_{18}H_{24}N_2O_4S$ (M.W. 364,47): calc.: C 59.54%; H 6.61%; N 7.81%; S 8.65%; found: 59.32%; 6.64%; 7.69%; 8.79%.

EXAMPLE 7

Ethyl 3-methyl-5-phenyl-5-N-piperidino-4-oxo-$\Delta^{2,\alpha}$-thiazolidine-acetate.

Ethyl 3-methyl-5-phenyl-4-oxo-$\Delta^{2,\alpha}$-thiazolidine-acetate, prepared in the manner described in Example 1, is brominated in a manner analogous to that described in Example 5 and then reacted in situ with piperidine. There are obtained (0.05 molar batch) 8.2 g. (45.6% of theory, over two stages) ethyl 3-methyl-5-phenyl-5-N-piperidino-4-oxo-$\Delta^{2,\alpha}$-thiazolidine-acetate which, after recrystallisation from ethanol, has a melting point of 173°–174° C.

Analysis: $C_{19}H_{24}N_2O_3S$ (M.W. 360.47): calc.: C 63.45% H 6.61%; N 7.81%; S 8.82%; found: 63.30%; 6.71%; 7.70%; 8.90%.

EXAMPLE 8

Ethyl 3-methyl-5-phenyl-5-N-pyrrolidino-4-oxo-$\Delta^{2,\alpha}$-thiazolidine-acetate.

28 g. (0.1 mol) ethyl 3-methyl-5-phenyl-4-oxo-$\Delta^{2,\alpha}$-thiazolidine-acetate are brominated in the manner described in Example 5. The carbon tetrachloride phase is evaporated in a vacuum and the residue obtained is recrystallised from cyclohexane. There are obtained 25.1 g. (69.4% of theory) ethyl 3-methyl-5-bromo-5-phenyl-4-oxo-$\Delta^{2,\alpha}$-thiazolidine-acetate which melts, with decomposition, at 96°–106° C.

Analysis: calc.: Br 22.4%; found: 22.0%.

The ethyl 3-methyl-5-bromo-5-phenyl-4-oxo-$\Delta^{2,\alpha}$-thiazolidine-acetate thus obtained is reacted in ether at 0° C. with pyrrolidine in a manner analogous to that described in Example 5. The yield (0.07 molar batch) is 12 g. (50% of theory) ethyl 3-methyl-5-phenyl-5-N-pyrrolidino-4-oxo-$\Delta^{2,\alpha}$-thiazolidine-acetate which, after recrystallisation from ethanol, melts at 95° C.

EXAMPLE 9

Ethyl 3-methyl-5-phenyl-5-diethylamino-4-oxo-$\Delta^{2,\alpha}$-thiazolidine-acetate.

10.7 g. (0.03 mol) ethyl 3-methyl-5-phenyl-5-bromo-4-oxo-$\Delta^{2,\alpha}$-thiazolidine-acetate are dissolved in 125 ml. dry ether and reacted at 8°–10° C. with 4.4 g. (0.06 mol) diethylamine in ethereal solution. Diethylamine hydrobromide formed is then separated off and the filtrate evaporated to dryness. The residue is recrystallised from isopropanol. Yield 3.3 g. (32% of theory) ethyl 3-methyl-5-phenyl-5-diethylamino-4-oxo-$\Delta^{2,\alpha}$-thiazolidine-acetate, which melts at 112° C.

Analysis: $C_{18}H_{24}N_2O_3S$ (M.W. 348.47): calc.: C 62.04%; H 6.94%; N 8.04%; S 9.20%; found: 62.12% 6.82%; 7.80%; 9.05%.

Pharmacological comparative experiments

EXAMPLE 10

Acute Toxicity

The acute toxicity of the thiazolidones according to the present invention was investigated on male mice (NMRI) with a body weight of 21–26 g. Before commencement of the experiment, the animals fasted for 24 hours but with water available ad libitum. There were 4 mice in each dosage group. The dosage was increased by a factor of 2. The test compounds were suspended in a 1% tragacanth mucilage and administered intragastrally by, means of a stomach probe. The amount of liquid administered was 0.2 ml./10 g. body weight. The animals were observed for a total of 7 days. Silymarin was used as standard substance. The $LD_{50}$ values determined are set out in the following Table I:

TABLE I

Acute toxicity of the thiazolidones according to the present invention in the 7 day test on mice

| active compound No. | mode of administration | $LD_{50}$ mg./kg. |
|---|---|---|
| 1 | i.g. | >1600 |
| 2 | i.g. | >1600 |
| 3 | i.g. | about 1600 |
| 4 | i.g. | >1600 |
| 5 | i.g. | >1600 |
| silymarin | i.g. | >1600 |

1 = ethyl 3-methyl-5-phenyl-5-N-piperidino-4-oxo-$\Delta^{2,}$-thiazolidine-acetate (Example 7)
2 = ethyl 3-methyl-5-phenyl-5-N-pyrrolidino-4-oxo-$\Delta^{2,}$-thiazolidine-acetate (Example 8)
3 = ethyl 3-methyl-5-ethyl-5-phenyl-4-oxo-$\Delta^{2,}$-thiazolidine-acetate (Example 1)
4 = ethyl 3-ethyl-5-phenyl-5-N-piperidino-4-oxo-$\Delta^{2,}$-thiazolidine-acetate (Example 3)
5 = ethyl 3-ethyl-5-phenyl-5-(methyl-β-hydroxyethylamino)-4-oxo-$\Delta^{2,}$-thiazolidine-acetate (Example 6)

Results

As can be seen from the results set out in the above Table I, the acute toxicity of the five compounds according to the present invention is very low. The $LD_{50}$ values of test compounds Nos. 1, 2, 4 and 5 are above 1600 mg./kg. The average toxicity of the standard substance silymarin is also found to be more than 1600 mg./kg. In the case of test compound No. 3, The $LD_{50}$ is about 1600 mg./kg.

EXAMPLE 11

Investigation of the anti-hepatotoxic action of the thiazolidones according to the present invention on rats with liver damage caused by carbon tetrachloride In this experiment, there was determined the period of narcosis in rats with liver damage caused by carbon tetrachloride after the administration of sodium hexobarbital, with and without treatment with the thiazolidones according to the present invention. Silymarin was used as standard substance since it is representative of the present state of the art with regard to compounds with an anti-hepatotoxic action.

The period of narcosis after the administration of sodium hexobarbital is substantially determined by the rate of metabolism of this compound in the liver. In the case of animals with liver damage caused by carbon tetrachloride, the period of hexobarbital narcosis is prolonged as a result of the influencing of the enzyme system of the liver breaking down foreign substances by radicals formed from carbon tetrachloride. These appear in exchange action with the enzyme system and block it for the breakdown of the barbiturate (see T. C. Butler, J. Pharmacol. exp. Therap., 311, 134/1961; T. F. Slater, Nature, 36, 209/1966; and R. O. Recknagel, Pharmacol. Rev., 19, 145/1967).

The determination of the period of narcosis in animals with liver damage caused by carbon tetrachloride gives, therefore, an indication regarding the functional state of the liver (see T. Balazs, and H. C. Grice, Toxicol. appl. Pharmacol., 5, 387/1963; and R. Megirian, J. Parmacol. exp. Therap., 144, 331/1964). This method can be used to determine substances with hepatoprotective properties since they counteract the prolongation of the period of narcosis of liver damage caused by carbon tetrachloride.

Method tail vein of the animals. The criterion for the period of narcosis was the time from the end of the hexobarbital injection up to the recovery of the position and standing reflexes. During the period of narcosis, the normal body temperature was maintained by means of heating lamps.

From the individual results of each investigational group, there was calculated the average values with the related standard deviations. In order to determine the influence of the thiazolidones according to the invention and of silymarin on the period of narcosis of animals with liver damage caused by carbon tetrachloride, the difference between the average period of narcosis of the control group with carbon tetrachloride liver damage and of the control group without carbon tetrachloride liver damage was taken as being 100 and the difference between the average period of narcosis of the substance group with carbon tetrachloride liver damage and the control group without liver damage was calculated as a percentage thereof. Student's test was used to examine the differences between the individual investigational groups for significance. The results of the comparative experiments are given in the following Table II:

TABLE II

| Compound No. | dosage mg/kg i.g. | period of narcosis in minutes | | | increase or decrease of period of narcosis as % of substance group | significance p = |
|---|---|---|---|---|---|---|
| | | control group without CCl$_4$ liver damage | control group with CCl$_4$ liver damage | compound group with CCl$_4$ liver damage | | |
| 1 | 150 | 18.10 ± 5.80 | 69.08 ± 20.36 | 52.75 ± 22.52 | − 34.66 | > 0.05 |
| 1 | 250 | 14.92 ± 4.52 | 87.83 ± 19.90 | 35.67 ± 13.76 | − 71.54 | < 0.001 |
| 2 | 250 | 19.50 ± 4.12 | 81.80 ± 26.51 | 34.83 ± 14.65 | − 75.39 | < 0.001 |
| 3 * | 75 | 18.10 ± 5.80 | 69.08 ± 20.36 | 31.67 ± 23.56 | − 73.38 | < 0.001 |
| 3 * | 150 | 17.00 ± 4.08 | 74.75 ± 21.09 | 15.75 ± 3.77 | − 102.16 | < 0.005 |
| 4 | 100 | 14.92 ± 4.52 | 87.83 ± 19.90 | 55.82 ± 21.91 | − 43.90 | < 0.001 |
| 4 | 200 | 14.67 ± 2.57 | 57.33 ± 15.26 | 26.00 ± 5.20 | − 73.44 | < 0.001 |
| 5 | 200 | 15.64 ± 3.93 | 73.00 ± 13.30 | 36.58 ± 9.62 | − 63.49 | < 0.001 |
| Silymarin | 100 | 23.42 ± 7.48 | 79.73 ± 22.75 | 90.92 ± 17.43 | + 19.87 | > 0.05 |
| Silymarin | 200 | 23.42 ± 7.48 | 79.73 ± 22.75 | 85.92 ± 16.41 | + 10.99 | > 0.05 |

*In this experiment, each experimental group only contained 4 animals.

The experimental animals used were male rats (SIV 50) with a body weight of 110–160 g. They were provided with a standard feed and water was available ad libitum. Each experimental group comprised 10 - 12 animals. The treatment with the thiazolidones according to the present invention and with silymarin took place, in each case, over a period of time of, in all, 4 days, the substances being administered daily suspended in tragacanth mucilate (2 ml./100g.), administration being intragastrally by means of a stomach probe. On the second day of the treatment, carbon tetrachloride was administered and on the fourth treatment day the period of narcosis was determined. The animals of two control groups, one of which received carbon tetrachloride and the other of which did not, received, during the same period of time, a daily dosage of 2 ml./100 g of tragacanth mucilage. Before administration of the carbon tetrachloride, the animals fasted for 16 hours. The carbon tetrachloride was administered in a dilution of 1:50 in sesame oil (1 ml. of the dilution/100 g. body weight). The animals of the control group without carbon tetrachloride liver damage received at the time when the other animals received the carbon tetrachloride, only sesame oil in the above-given volume.

For the determination of the period of narcosis, 70 mg./kg. of a freshly prepared sodium hexobarbital solution (1 ml./100 g.) were injected in one minute into the Results As can be seen from Table II, liver damage in rats caused by carbon tetrachloride leads to a marked prolongation of the period of narcosis in comparison with control animals without carbon tetrachloride liver damage. The statistical calculation gave, in all experiments, a highly significant difference ($p = < 0.001$) between the two control investigational groups.

The five thiazolidones according to the present invention all bring about, as can be seen from Table II, in the case of intragastral administration for 4 days, a clear reduction of the period of narcosis in the case of carbon tetrachloride liver damaged rats in comparison with the results of the corresponding liver damaged control groups without treatment.

This anti-hepatotoxic action of the thiazolidones according to the present invention is highly sugnificant as is shown by the last column of Table II.

However, silymarin, which was tested in dosages of 100 and 200 mg./kg., did not result in a decrease of the period of narcosis of carbon tetrachloride liver damaged animals. Indeed, the period of narcosis of carbon tetrachloride liver damaged animals which had been treated with silymarin even showed a slight, although not significant, percentage increase in comparison with untreated liver damaged animals.

Since the testing of the acute toxicity of the thiazolidones according to the present invention gave, in all cases, LD$_{50}$ values of 1600 mg./kg. or more and the anti-hepatotoxic actions in the carbon tetrachloride test model even occurred in the case of substantially lower dosages than of silymarin, all five compounds provide a very good therapeutic spectrum.

EXAMPLE 12

Investigation of the anti-hepatotoxic action of the thiazolidones according to the present invention in mice with liver damage caused by α-amanitine.

As a further animal experimental test model for the testing of the anti-hepatotoxic actions of pharmaceuticals, use is made of the liver damage in mice produced by α-amanitine.

Since it is extremely difficult to obtain α-amanitine in sufficient amounts, only a small amount of α-amanitine was available for these experiments so that the experiments could only be carried out to a very limited extent.

Method

The influence of Compounds Nos. 1 and 4 was determined on the survival rate of mice with liver damage brought about by α-amanitine. As standard substance, there was again used silymarin which was tested by us in the dosage found to be effective by Hahn et al. (Arzneimittel Forschung, 18, 697/1968) as an anti-hepatotoxic in the same experimental procedure.

Each experimental group consisted of 25 animals. The test substances were administered daily over a period of 6 days, administration being intragastrally in a tragacanth mucilage (0.2 ml./10 g. body weight), using a stomach probe. Animals of the untreated liver damaged control group only received, over the whole of the same period of time, a daily dosage of tragacanth mucilage.

The intraperitoneal administration of, in each case, 0.3 mg./kg. α-amanitine took place in all experimental groups on the second day of the experiment. The dosage of α-amanitine was so chosen that the mortality rate of the untreated animals remained below 100%. The survival rate of the animals of all experimental groups was monitored daily for a total period of 14 days. The statistical comparison of the survival rate took place according to the Vierfelder α$^2$ test. The comparative values obtained are set out in the following Table III:

TABLE III

Influencing of the survival rate of α-amanitine liver damaged mice by thiazolidones according to the present invention and by silymarin

| compound No. | dosage mg/kg/ day | survival rate in % of α-amanitine liver damaged animals untreated | survival rate in % of α-amanitine liver damaged animals treated | significance p |
|---|---|---|---|---|
| 1 | 2 × 250 | 52 | 92 | 0.001 |
| 4 | 2 × 250 | 52 | 100 | < 0.001 |
| silymarin | 1 × 100 | 36 | 32 | > 0.05 |

As can be seen from the results given in Table III, the two tested compounds according to the present invention also show, in this test model, a superior anti-hepatotoxic effect.

A treatment with Compound No. 1 clearly increases the survival rate of α-amanitine liver damaged mice with a significance of 0.001 in comparison with untreated control animals. Compound No. 4 even increases the survival rate of the animals by 100%. This effect as statistically highly significant. The increase of the survival rate of α-amanitine liver damaged animals found by Hahn (loc. cit.) could not be confirmed by our experiments. As can be seen from Table III, silymarin does not bring about an increase of the survival rate.

We claim:

1. A 5-Phenyl-thiazolidin-4-one derivative of the formula:

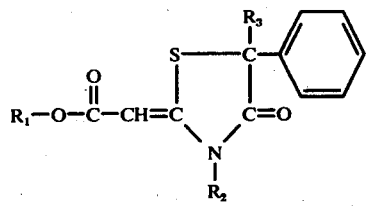

wherein R$_1$ is —CH$_2$CH$_3$; and
wherein R$_2$ is —CH$_3$, or —CH$_2$CH$_3$; and
wherein R$_3$ is 2-diethylamino ethyl, N-piperidino, methyl, β-hydroxyethylamino, N-pyrrolidino, or diethylamino.

2. The derivative according to claim 1 wherein R$_2$ is —CH$_3$, and R$_3$ is 2-diethylamino ethyl, and which is ethyl 3-methyl-5-phenyl-5-(2-diethylaminoethyl)-4-oxo-Δ$^{2,\alpha}$-thiazolidine-acetate.

3. The derivative according to claim 1 wherein R$_2$ is —CH$_2$CH$_3$, and R$_3$ is N-piperidino, and which is ethyl 3-ethyl-5-phenyl-5-N-piperidino-4-oxo-Δ$^{2,\alpha}$-thiazolidine-acetate.

4. The derivative according to claim 1 wherein R$_2$ is —CH$_2$CH$_3$, and R$_3$ is methyl-β-hydroxyethylamino, and which is ethyl 3-ethyl-5-phenyl-5-(methyl, β-hydroxyethylamino)-4-oxo-Δ$^{2,\alpha}$-thiazolidine-acetate.

5. The derivative according to claim 1 wherein R$_2$ is —CH$_3$, and R$_3$ is N-piperidino, and which is ethyl 3-methyl-5-phenyl-5-N-piperidino-4-oxo-Δ$^{2,\alpha}$-thiazolidine-acetate.

6. The derivative according to claim 1 wherein R$_2$ is —CH$_3$, and R$_3$ is N-pyrrolidino, and which is ethyl 3-methyl-5-phenyl-5-N-pyrrolidino-4-oxo-Δ$^{2,\alpha}$-thiazolidine-acetate.

7. The derivative according to claim 1 wherein R$_2$ is —CH$_3$, and R$_3$ is diethylamino, and which is ethyl 3-methyl-5-phenyl-5-diethylamino-4-oxo-Δ$^{2,\alpha}$-thiazolidine-acetate.

8. A 5-phenyl-thiazolidin-4-one of the formula:

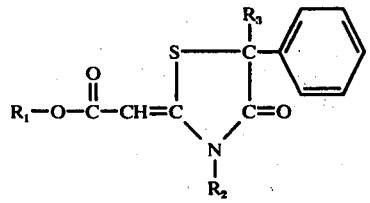

wherein R$_1$ is methyl or ethyl; R$_2$ is methyl or ethyl; and R$_3$ is piperidino, or pyrrolidino.

* * * * *